(12) United States Patent
Harder et al.

(10) Patent No.: US 6,689,059 B2
(45) Date of Patent: Feb. 10, 2004

(54) APPARATUS FOR THE IMPLEMENTATION OF A PHYSIOLOGICALLY CONTROLLED MEASUREMENT AT A LIVING SUBJECT

(75) Inventors: Martin Harder, Nuremberg (DE); Gerhard Seng, Herzogenaurach (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/059,742

(22) Filed: Jan. 29, 2002

(65) Prior Publication Data
US 2002/0103422 A1 Aug. 1, 2002

(30) Foreign Application Priority Data
Feb. 1, 2001 (DE) .......................... 101 04 451

(51) Int. Cl.⁷ .............................. A61B 5/00; A61B 5/05; A61B 5/04
(52) U.S. Cl. .................... 600/300; 600/427; 600/523
(58) Field of Search ................ 600/300, 523, 600/407, 425, 427

(56) References Cited

U.S. PATENT DOCUMENTS 6,224,549 B1 * 5/2001 Drongelen .................. 600/300
6,370,430 B1 * 4/2002 Mika et al. .................. 607/25

* cited by examiner

Primary Examiner—Eric F. Winakur
Assistant Examiner—David J. McCrosky
(74) Attorney, Agent, or Firm—Schiff Hardin & Waite

(57) ABSTRACT

An apparatus for the implementation of a physiologically controlled measurement at a living subject has a signal acquisition arrangement for acquiring a physiological signal of the subject, a display for the graphic display of a time curve of the physiological signal, and a time-setting arrangement for setting at least one relative point in time that is referenced to the time curve of the physiological signal and that is to be employed for the control of the time sequence of the measurement. The display is configured for also graphically displaying the at least one relative point in time in its temporal relationship to the physiological signal, particularly by mixing at least one time bar in the displayed image. Quick visual monitoring of the relative points in time that are set is thus possible.

7 Claims, 2 Drawing Sheets

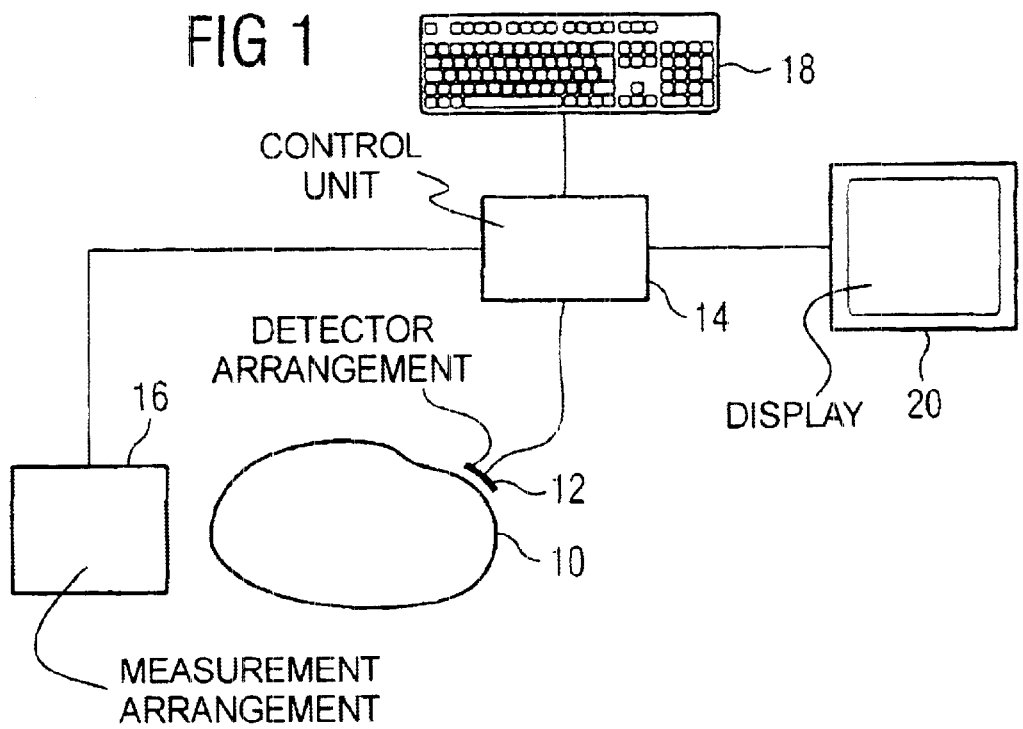
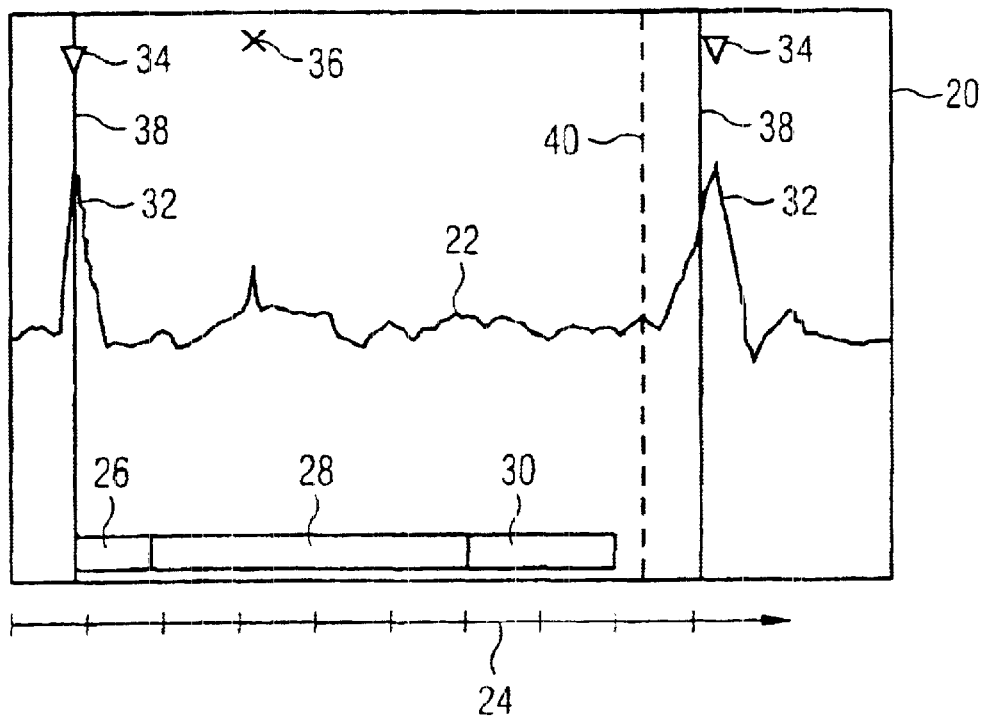

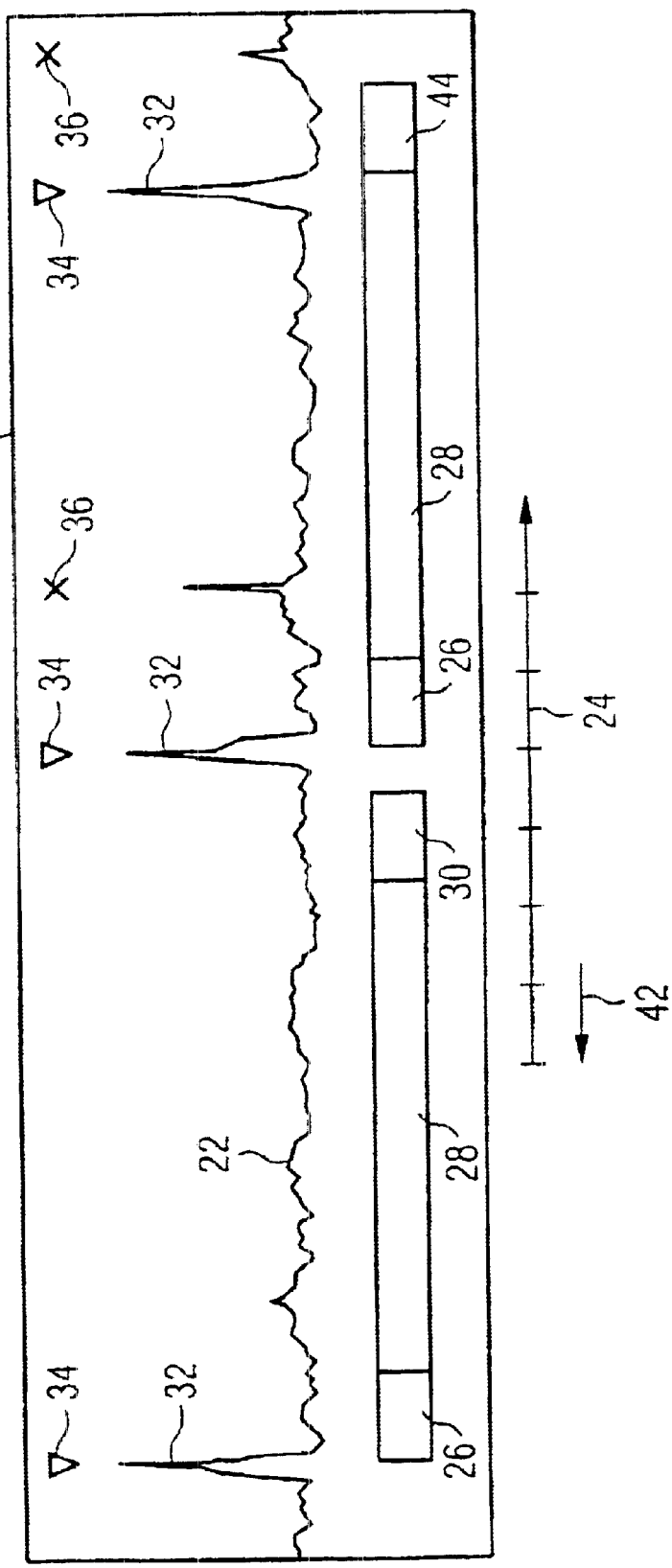

APPARATUS FOR THE IMPLEMENTATION OF A PHYSIOLOGICALLY CONTROLLED MEASUREMENT AT A LIVING SUBJECT

BACKGROUND OF THE INVENTION

1. Field of the Invention

The present invention is directed to an apparatus for the implementation of a physiologically controlled measurement at a living subject.

2. Description of the Prior Art

In a number of examinations of living subjects, meaningful and diagnostically relevant measurements are possible only at specific points in time or during specific phases within a physiological cycle. In computer-tomographic examinations of internal organs that, for example, move in the rhythm of the heart beat or respiration, it can be easily understandable that only slice projections that were acquired during comparable phases of the organ movement can be meaningfully compiled to form a tomography image that is capable of being interpreted. Such measurements therefore are temporally controlled according to a suitably selected physiological signal. One or more relative points in time that are utilized for the time-control of the measurement are thereby defined on the basis of the physiological signal.

Methods referred to as triggered methods are known for defining these relative points in time. In these methods, a trigger pulse in the physiological signal is employed as a reference time. The relative points in time are then defined in temporal reference to this trigger pulse. Their definition ensues, for example, by indicating a waiting time (delay time) after every trigger pulse and by defining the length of an actual measurement time window (scan acquisition window) that begins after the delay time has passed and within which the measured data are to be registered. The parameters of "delay time" and "scan acquisition window" are usually entered in numerical form as input by the user via a keyboard. The scan acquisition window is derived from a number of other parameters that the user can set, for instance on the basis of a number of sub-measurements that are to be implemented per scan acquisition window. The length of the scan acquisition window then is derived from a multiplication of this number of sub-measurements by the time duration (repetition time) that is to be expended for every sub-measurement and which can likewise may be potentially set.

Further, there are methods referred to as gating methods. In these, a time window (gate) controlling the measurement is usually defined by amplitude thresholds of the physiological signal. When the physiological signal passes through such a threshold, then this is considered as a switch-on or switch-off time of the time window. Given a breathing-controlled measuring method, for example, a suitable percentage of the respiratory motion can be selected as threshold.

A problem associated with physiologically controlled measurements is that the signal parameters of the physiological signal employed as reference are often not constant but instead can be subject to considerable fluctuations. In particular, the signal parameters, for instance the signal cycle or the maximum or the average signal amplitude, can change between one phase of the measurement preparation and the phase of the actual measurement implementation, due, for example, to an increase of the heartbeat or respiration rate. When suitable values for the aforementioned parameters of waiting time, length of the scan acquisition window, threshold height and the like have been set in the preparatory phase, these parameter values may no longer be suitable in the following implementation phase of the measurement, and lead to measurement results that have little diagnostic utility.

SUMMARY OF THE INVENTION

It is an object of the present invention to provide a simple arrangement for reliably monitoring whether the (at least one) relative point in time to be employed for the time control of the measurement is still suitable—as soon as it has been set and compared to the current curve of the physiological signal—in order to be able to meaningfully implement the measurement.

This object is achieved in accordance with the invention in an apparatus for the implementation of a physiologically controlled measurement in a living subject, having a signal acquisition arrangement for acquiring a physiological signal of the subject, display for the graphic display of a time curve of the physiological signal, and a time-setting unit which sets at least one relative point in time that is referenced to the time curve of the physiological signal and that is to be employed for the control of the time sequence of the measurement.

In accordance with the invention the display is configured for also graphically displaying the at least one relative point in time in its temporal relationship to the physiological signal.

Due to the simultaneous, graphic display of the at least one relative point in time, the invention makes it possible for the user to continuously visually check whether the respective relative point in time has been suitably set or must be adapted, by comparing the displayed relative point in time to the displayed, current signal curve of the physiological signal. This is possible at first glance because the relative point in time is displayed in temporal relationship to the physiological signal, i.e. based on the same time scale. A mere numerical value for the relative point in time is thus not merely mixed in the displayed information on the screen; rather, the time position of the relative point in time relative to the physiological signal is shown.

In a preferred embodiment of the invention, at least two different relative points in time can be set with the time-setting arrangement, with the display being configured for graphically displaying a time window lying between two relative points in time in temporal relationship to the physiological signal. Further, the display can be configured for graphically displaying a time window lying between a relative point in time and a reference point in time of the physiological signal in its temporal relationship to the physiological signal. The time windows can be especially easily visually recognized in an embodiment wherein they are displayed in the form of a time bar. In the case of a number of simultaneously displayed time windows, for example, different colors for the time bars can be employed.

It can be desirable in some instances for the display to display the physiological signal and the at least one relative point in time with a stationary time axis. In other instances, however, it is also desirable that the display to display the physiological signal and the at least one relative point in time with a moving time axis.

DESCRIPTION OF THE DRAWINGS

FIG. 1 is a schematic block diagram of the measurement arrangement according to the invention.

FIG. 2 shows an example of a graphic display on a picture screen of the measurement instrument during a measurement preparation phase in accordance with the invention.

FIG. 3 shows an example of a graphic display on the picture screen during a measurement implementation phase in accordance with the invention.

DESCRIPTION OF THE PREFERRED EMBODIMENTS

In FIG. 1, the body of the human or animal to be examined is referenced 10. A detector arrangement 12 registers a physiological signal of the body 10 and conducts this to an electronic measurement control unit 14. For example, the detector arrangement 12 can register the electrical heart currents as employed for an electrocardiogram (ECG) as the physiological signal. Alternative possibilities are the respiratory motions of the body, pulse, diaphragm movements, etc. The measurement control unit 14 employs the physiological signal for the time control of tomographic or other arbitrary measurements that are implemented at the body 10 with a measurement arrangement 16. The measurement arrangement 16 can, for example, be a magnetic resonance tomography apparatus or an x-ray computed tomography apparatus. When such tomographic examinations are undertaken at cyclically (though not necessarily regularly) moving internal organs such as, for example, the heart or lung, then tomographic images that are diagnostically relevant are obtained only when the number of individual measurements that are needed for the reconstruction of the tomographic image are implemented during corresponding cycle phases, i.e., for example, during phases when the heart is at rest. For this reason, the measurement control unit 14 controls the measurement arrangement 16 such that its measuring activities occur only during a specific measurement time window within the cycle of the detected physiological signal.

This measurement time window is not defined by the measurement control unit 14 itself. On the contrary, the user defines the length and relative position of the measurement time window (i.e., starting and ending time) within the signal cycle by the user entering values for one or more parameters via a keyboard 18 connected to the measurement control unit 14. For example, these parameters can be: one or more amplitude thresholds of the physiological signal (in gating methods) or a waiting time until the beginning of the measurement time window after a pulse spike of the physiological signal employed as a trigger, the number of individual measurements to be implemented during the measurement time window and the measurement time to be made available per individual measurement (given trigger methods).

The user can then graphically view the measurement time window defined by entering the parameter values on a picture screen of a display 20 driven by the measurement control unit 14. The physiological signal as well as the measurement time window are mixed in the image on the display 20, the latter in such a way that its time position and extent relative to the physiological signal can be immediately seen. Preferably, the measurement time window is represented by a bar or a line that extends in the same time scale as the physiological signal along the latter. If the user is not satisfied with the position and size of the measurement time window, the user can correct the parameter values until the measurement time window that has been set is the one desired.

FIG. 2 shows an example graphics on the display 20 in the case of an ECG-triggered measurement. An ECG signal 22 thereby serves as physiological reference signal. This is displayed on the display 20 along a horizontal time axis 24. In addition to the ECG signal 22, an arrangement of, preferably, differently colored horizontal bars 26, 28, 30 is also displayed on the display 20. The middle bar 28 thereof represents the measurement time window that has been set for the implementation of the measurement, the left bar 26 represents a time delay after a R-spike 32 of the ECG signal employed as trigger pulse, and the right bar 30 denotes a remaining time. This remaining time is derived from the difference between a maximum time duration (user acquisition window) that is available overall and is prescribed by the user as additional parameter and the sum of time delay and measurement time window.

In a phase preparatory to a measurement, the displayed physiological signal curve 22 is cyclically updated, for example after every trigger pulse or respectively following a predetermined time duration, for instance respectively every three seconds. At each updating, the curve 22 is re-plotted, whereby the point in time of the trigger pulse 32 (the middle spike of the QRS complex in the ECG signal) remains standing at a fixed point in the display window of the picture screen 20. Given gating methods that, for example, employ a respiratory signal as physiological reference signal, the reaching of a threshold can be accepted as fixed point. The stationary but repeatedly updated image of the physiological signal thus arises on the display 20 given a stationary time axis 24. As a result of the surveyable, additional mixing-in of the bars 26, 28, 30, with reference to which the user can recognize the current setting of the measurement parameters, it is especially easy for the user to find the most suitable values for these parameters.

In the exemplary graphic of FIG. 2, arrows 34 indicate two successive R-spikes in the ECG signal 22 that are employed as trigger pulses; a cross 36 references a recognized extra systole. Two vertical lines 38—the left line thereof lying at the time location of the trigger pulse 32 employed as fixed point for the graphic display—indicate the average interval between two successive R-spikes of the ECG signal 22. A region between the left line 38 and a broken line 40 represents an overall time window ("system acquisition window") recommended to the user on the basis of a long-term statistics and within which the measurement events should occur. This system acquisition window is derived from the average R—R interval reduced by twice standard deviation. The latter corresponds to the region between the line 40 and the right line 38. For better visualization, the system acquisition window and the region of twice the standard deviation can have differently colored backgrounds.

The signal curve 22 with the bars 26, 28, 30 is displayed on the picture screen of the display 20 not only during preparation for the measurement but also during the implementation of the actual measurement. Separate display windows for the preparation for the measurement and the measurement implementation can thereby be established on the display 20 in order to already begin preparing a subsequent measurement simultaneously with the implementation of a measurement. FIG. 3 shows an example of a graphic display on the display 20 for the measurement implementation. Corresponding elements are thereby referenced with the same reference characters as in FIG. 2. During the measurement implementation, the signal curve 22 is preferably plotted in continuous form, i.e. is pushed through the display window (along an arrow 42 from right to left here) with a moving time axis 24 as close as possible to real time. Simultaneously, the bars 26, 28, 30 also are plotted in terms of their relative position and extent with reference to the signal curve 22 and are likewise moved through the display window. The user can thus very easily recognize whether the setting of the parameters implemented in the phase of preparing for the measurement is suitable or, for example, requires adaptation due to a faster heart beat.

The next trigger pulse in the form of the R-spike 32 of the ECG signal 22 may already (unexpectedly) occur before the expiration of the measurement time window that has been set (correspondingly before the end of the bar 28). This is illustrated in the right half of FIG. 3. This case can be visualized for the user by a bar 44, that extends up to the end of the user acquisition window set by the user, being mixed in beginning with the point in time of the interruption. A signal color, for example red, may be specifically reserved for this purpose. The user can thus immediately recognize when the heart rhythm or, in general, the rhythm of the physiological signal, increases so greatly that the measurement should be interrupted and should only be restarted after modified parameter values have been set.

Numerical values for those points in time that mark the starting or ending points in time of the bars, also can be displayed on the picture screen 20 in addition to the bars 26, 28, 30.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for obtaining a physiologically controlled measurement at a living subject, comprising:

a signal acquisition arrangement, adapted for interaction with a living subject, for continually acquiring a physiological signal from the living subject, said physiological signal having a current time curve associated therewith;

a time-setting arrangement connected to said signal acquisition arrangement for allowing manual setting of at least two different points in time referenced to said current time curve for controlling a time sequence of a measurement to be subsequently implemented at said living subject; and a display connected to said signal acquisition arrangement and said time-setting arrangement for graphically displaying said current time curve of said physiological signal and for automatically determining and graphically displaying a time window between said at least two points in time in a temporal relationship to said current time curve of said physiological signal, said time window indicating a time span within which measurement should occur.

2. An apparatus as claimed in claim 1 wherein said display displays said time window as a time bar.

3. An apparatus as claimed in claim 1 wherein said display also displays a reference point in time, and wherein said display graphically displays a time window between said point in time and said reference point in a temporal relationship to said time curve of said physiological signal.

4. An apparatus as claimed in claim 3 wherein said display displays said time window as a time bar.

5. An apparatus as claimed in claim 1 wherein said display displays said physiological signal and said at least one point in time with a stationary time axis.

6. An apparatus as claimed in claim 1 wherein said display displays said physiological signal and said at least one point in time with a moving time axis.

7. An apparatus as claimed in claim 1 wherein said measurement is a tomographic measurement, and wherein said display automatically determines and graphically displays a time window indicating an optimum time span within which said tomographic measurement should occur.

* * * * *